US005683678A

United States Patent [19]
Heckert et al.

[11] Patent Number: 5,683,678
[45] Date of Patent: Nov. 4, 1997

[54] ORAL COMPOSITIONS

[75] Inventors: David Clinton Heckert; Richard Joseph Sunberg, both of Oxford, Ohio

[73] Assignee: The Procter & Gamble Company, Cincinnati, Ohio

[21] Appl. No.: 401,316

[22] Filed: Mar. 9, 1995

[51] Int. Cl.⁶ .................... A61K 7/16; A61K 7/18; A61K 7/26; A61K 35/78
[52] U.S. Cl. .................... 424/52; 424/49; 424/58; 424/195.1
[58] Field of Search .................... 424/49–58, 195.1

[56] References Cited

U.S. PATENT DOCUMENTS

| | | | |
|---|---|---|---|
| 3,266,903 | 8/1966 | Jurd | 99/103 |
| 3,720,230 | 3/1973 | Stockstill | 137/564.5 |
| 4,105,675 | 8/1978 | Iacobucci et al. | 260/345.2 |
| 4,105,758 | 8/1978 | Schreiber | 424/49 |
| 4,172,902 | 10/1979 | Asen et al. | 426/250 |
| 4,208,434 | 6/1980 | Iacobucci et al. | 426/72 |
| 4,211,577 | 7/1980 | Wallin | 106/288 |
| 4,229,439 | 10/1980 | Majoie | 424/180 |
| 4,255,563 | 3/1981 | Wakihira et al. | 536/8 |
| 4,258,055 | 3/1981 | Lietti et al. | 424/283 |
| 4,320,009 | 3/1982 | Hilton et al. | 210/651 |
| 4,374,123 | 2/1983 | Luccarelli et al. | 424/49 |
| 4,376,781 | 3/1983 | Lietti et al. | 424/283 |
| 4,386,064 | 5/1983 | Klemarczyk et al. | 424/49 |
| 4,413,004 | 11/1983 | Lietti et al. | 424/283 |
| 4,698,360 | 10/1987 | Masquelier | 514/456 |
| 4,707,360 | 11/1987 | Brasey | 424/94.1 |
| 4,786,510 | 11/1988 | Nakel et al. | 426/74 |
| 4,786,518 | 11/1988 | Nakel et al. | 426/531 |
| 4,797,421 | 1/1989 | Ariga et al. | 514/844 |
| 4,863,956 | 9/1989 | Gabetta et al. | 514/453 |
| 4,925,870 | 5/1990 | Gabetta et al. | 514/453 |
| 4,925,871 | 5/1990 | Gabetta et al. | 514/453 |
| 4,971,811 | 11/1990 | Strobel et al. | 426/50 |
| 4,971,813 | 11/1990 | Strobel et al. | 426/51 |
| 4,999,423 | 3/1991 | Ioaka | 536/4.1 |
| 5,108,761 | 4/1992 | Andon et al. | 426/2 |
| 5,200,186 | 4/1993 | Gabetta et al. | 424/195.1 |

(List continued on next page.)

FOREIGN PATENT DOCUMENTS

| | | |
|---|---|---|
| 0494512A2 | 7/1992 | European Pat. Off. . |
| 2230116 | 1/1973 | Germany . |
| 2035880 C1 | 5/1993 | Romania . |

OTHER PUBLICATIONS

Pollock et al. Arch. Dis. Child (England) 65(1):74–77 Jan. 1990 Effect of Artificial Food Colours on Childhood Behavior.

Silbergeld et al. Bull. N.Y. Acad. Med USA 58(3):275–293 1982 Artificial Food Colors and Childhood Behavior Disorders.

Mailmain et al. Appl. Res. Ment. Retard. US 2(4):297–313 1981 Food Additives and Developmental Disorders.

Lockey Ann Allergy US 38(3):206–210 Mar. 1977 Hypersensitivity to F.DC Yellow #5 & Other Dyes.

Hawley et al. J. Appl. Nutr. (USA) 26(4):57–61 1974 Sensitivity to Food Dyes in Hyperkinetic Children.

Cripppa et al CA. 94:145335 of Ger DE 3027933 (Feb. 26, 1981).

Lietti et al. GA. 88:177226 of Ger DE 2740346 (Mar. 9, 1978).

Kashket et al. Arch. Oral. Biol. 30(11–12) 821–826 (1985) GA. 104:128611.

Halopainen et al. Acta Pharm. Fenn. 97(4): 197–202 (1988) GA. 111:36508.

Iwahata et al. JP 012 42 066 (Sep. 27, 1989) GA. 113:64562. In–Vitro Inhibition of Glucosyltransferase from the Dental Plaque Bacterium *Streptococcus Mutans* by Common Beverages and Food Extracts.

*Archs oral Biol.* vol. 30, No. 11/12, 1985, pp. 821–826 S. Kashket, V. J. Paolino, D. A. Lewis and J. van Houte, Forsyth Dental Center, Boston, MA 02115.

Use of HPLC to Monitor Juice Authenticity *Food Technology* Apr. 1984, pp. 88–91 Elia D. Coppola.

Microbial Inhibitors of Cranberries *Journal of Food Science* vol. 51, No. 4, 1986, pp. 1009–1013 Aref G. Marwan and Charles W. Nagel..

Apha Hanbook of Non–Prescription Drugs 10th ed 1993 pp. 413, 415 Toothpaste Table pp. 809–812.

Rebecca Christian "The Way to a Natural Smile for Those Who Prefer to Avoid Chemicals in Toothpaste" Organic Gardening 27(8) 112–117 Aug. 1980.

Bernice Kanner New York Magazine Mar. 29, 1982 12–18 On Madison Avenue The Gelling of America–"The Latest Toothpastes".

Deborah Blumenthal N.Y. Times Magazine Jun. 20, 1982:68–69"Taking a Pasting. "

Consumer Reports Mar. 1986:142–149"Toothpastes".

Ad week's Marketing Week May 25, 1992 p. 17 "Green Products that Do Double Duty".

Product Alert Mar. 23, 1992, Tom's of Maine Natural Toothpaste with Fluoride for Children.

Washington Post(DC) Nov. 5, 1986 p. C1 "It's Natural" vs. Big Guys in Toothpaste.

Jereski, Laura Forbes vol. 143 No. 7 p. 802 Apr. 3 1989 Tom's of Maine–Hearts, Minds and Market Share.

Boyers, Karla Association Management vol. 48, No. 2, p. 44(6) Feb. 1996 Tom's of Maine, Inc.

Gorman's New Product News vol. 28, No. 4, p. 40(7) May 11, 1992.

PR Newswire Mar. 25, 1992 "Getting Kids to Brush –Naturally" McMath Adweek's Marketing Week vol. 31 No. 16 p. 49(1) Apr. 16, 1990.

*Primary Examiner*—Shep K. Rose
*Attorney, Agent, or Firm*—Douglas C. Mohl; David K. Dabbiere; Jacobus C. Rasser

[57] ABSTRACT

The present invention relates to oral compositions containing cranberries or parts of cranberries, such as cranberry extract, or a mixture of such materials and other antibacterial/antimicrobial agents. The invention also relates to methods of treating plaque/gingivitis and other periodontal diseases as well as dental calculus and caries.

3 Claims, No Drawings

U.S. PATENT DOCUMENTS

| | | | |
|---|---|---|---|
| 5,232,709 | 8/1993 | Saltman et al. | 424/630 |
| 5,320,841 | 6/1994 | Seghizzi et al. | 424/195.1 |
| 5,389,387 | 2/1995 | Zuniga et al. | 426/74 |
| 5,401,524 | 3/1995 | Burkes et al. | 426/590 |
| 5,422,128 | 6/1995 | Burkes et al. | 426/74 |
| 5,431,940 | 7/1995 | Calderas et al. | 426/330.3 |
| 5,464,619 | 11/1995 | Kuznicki et al. | 424/195.1 |
| 5,474,774 | 12/1995 | Walker et al. | 424/195.1 |
| 5,516,535 | 5/1996 | Herkert et al. | 426/2 |
| 5,525,341 | 6/1996 | Walker et al. | 424/195.1 |
| 5,571,441 | 11/1996 | Andon et al. | 252/1 |

ORAL COMPOSITIONS

TECHNICAL FIELD

The present invention relates to oral compositions containing cranberries or parts of cranberries, such as cranberry extract or other members of the Ericaceae family, as antiplaque, anticalculus and anticaries agents.

Plaque induced diseases, including periodontitis and gingivitis, are believed to involve anaerobic bacterial infections. Periodontal disease affects the periodontium, which is the investing and supporting tissue surrounding a tooth (i.e., the periodontal ligament, the gingiva, and the alveolar bone). Gingivitis and periodontitis are inflammatory disorders of the gingiva and the periodontal ligament, respectively. Gingivosis and periodontosis are more severe conditions involving degenerative disorders of the tissue. Combinations of inflammatory and degenerative conditions are termed periodontitis complex.

Periodontal disease is a major cause of tooth loss in adults. Tooth loss from periodontal disease is a significant problem beginning at age 35, but even by age 15 it is estimated that about 4 out of 5 persons already have gingivitis and 4 out of 10 have periodontitis.

While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these microorganisms must be suppressed by some means other than simple mechanical scrubbing. Towards this end, there has been a great deal of research aimed at developing therapeutic dentifrices, mouthwashes, and methods of treating periodontal disease which are effective in suppressing these microorganisms.

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. This is undesirable from an aesthetic standpoint.

A wide variety of chemical and biological agents have been suggested in the art to retard calculus formation or to remove calculus after it is formed. Mechanical removal of this material periodically by the dentist is, of course, routine dental office procedure.

The chemical approach to calculus inhibition generally involves chelation of calcium ions and/or crystal growth inhibition which prevents the calculus from forming and/or breaks down mature calculus by removing calcium.

An observation that cranberry juice and other beverages could inhibit enzymes from plaque is noted in S. Kasket et al, "In-vitro Inhibition of Glucosyltransferase From Plaque Bacterium Streptococcus Mutans by Common Beverage and Food Extracts", *Arch Oral Biology*, Vol 30, No. 11/12, pp 821–826, 1985.

However, the S. Kasket et al disclosure suggests that "the effects of the fruit juices (tested in their system) were attributable mainly to the inhibition of the glucosyltransferase by the endogenous fructose and glucose."

Surprisingly, we have discovered that cranberry extract inhibits glucosyltransferase well beyond what can be attributed to sugars.

This finding is consistent with cranberry providing an anticaries benefit.

Although there have been a number of approaches disclosed for combating periodontal disease, caries and calculus, there is still the desire and need to develop improved products possessing such properties. Additionally, although the above described article discloses an in-vitro test with cranberry juice, there is no suggestion to form topical compositions such as mouthwashes, toothpastes, chewing gums and lozenges or that such compositions would be effective. This is due in large part to the short residence time of such compositions in the mouth. Additionally, the many other components in such compositions could affect the release of the active.

It is an object of the present invention to provide compositions which deliver antiplaque, antigingivitis, antiperiodontitis, anticaries and anticalculus benefits employing cranberries or parts of cranberries, such as extracts or juices. Additionally, other members of the Ericaceae family may be used, such as blueberries.

It is a further object of the present invention to produce an effective product using a mixture of above-mentioned materials and other antibacterial/antimicrobial agents.

It is still a further object of the present invention to provide anticalculus products which are cosmetically acceptable and do not inhibit remineralization of the teeth.

It is still a further object of the present invention to provide effective methods for combating calculus, plaque, caries, gingivitis and periodontitis.

These and other objects will become more clear from the detailed description which follows.

All percentages and ratios used herein are by weight unless otherwise specified. Also all measurements referred to herein are made at 25° C. in the composition or on the pure material unless otherwise specified.

SUMMARY OF THE INVENTION

The present invention embraces an oral composition comprising:

(a) a safe and effective amount of an agent selected from the group consisting of cranberries, parts of cranberries, other members of the Ericaceae family and mixtures thereof; and (b) an acceptable carrier.

The present invention also encompasses a method for retarding development of dental calculus, plaque, caries, gingivitis and periodontitis.

DETAILED DESCRIPTION OF THE INVENTION

The compositions of the present invention comprise cranberry extract in a suitable oral care carrier.

By "safe and effective amount" as used herein means sufficient amount of material to provide the desired benefit while being safe to the hard and soft tissues of the oral cavity.

By the term "comprising", as used herein, is meant that various additional components can be conjointly employed in the compositions of this invention as long as the listed materials perform their intended functions.

By the term "acceptable carrier", as used herein, is meant a suitable carrier which can be used to apply the present agent(s) to the oral cavity without undue toxicity, irritation, allergic response and the hike, commensurate with a reasonable benefit/risk ratio.

Cranberries, Parts of Cranberries, such as Extracts of Cranberries and Other Members of the Ericaceae Family The materials useful in the present invention are those listed in the heading, as well as the specific chemicals which are present in those materials. Cranberry extracts are the preferred materials for use in the present invention and extraction can be done in a number of different ways, such as is shown in the examples.

Agents which may provide activity from cranberries are the pigments found in the skins of the berries.

Cranberry pigments fall into two main groups. The plastid pigments are associated with protoplasmic structure and include water-insoluble chlorophylls, carotene, and xanthophyll. The sap soluble pigments include the anthocyanins and anthoxanthins. The anthoxanthins, or yellow flavonoids of cranberries, comprise quercetin-3-galactoside as the major pigment, followed by quercetin-3-rhamnoside, quercetin-3-arabinoside, quercetin, myricetin-3-arabinoside, and myricetin-3-digalactoside. The flavonoid pigments are of much greater importance than the water-insoluble pigments not only because they are present in much greater quantities, but because the flavonoids, particularly anthocyanins, are more stable than the chlorophylls or carotenoids.

Anthocyanins are by far the most important pigment of cranberries. Anthocyanin as is derived from the Greek words for flower and blue, and introduced in 1835 by the French botanist L. C. Marquart to describe the blue pigment of cornflowers. It has since been used in wider sense to include a large group of water soluble pigments of similar structure comprising the red, violet, and blue pigments of plant materials, since it was recognized that these pigments were merely different forms of the same substance. Anthocyanins are all based chemically on a single aromatic structure a 3, 5, 7, 3', 4'-pentahydroxy flavylium cation, cyanidin.

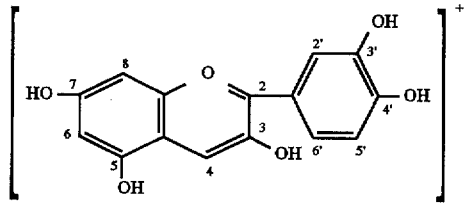

It consists of two benzene rings A and B joined by a 3 carbon link formed into a pyrone ring, which is considered associated with the B ring. The different classes of flavonoid compounds differ from one another only by the state of oxidation of this 3 carbon link. In the anthocyanins the state of oxidation may be represented as:

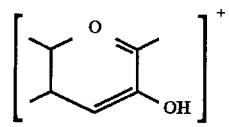

Anthocyanins are glycosidic, or sugar containing, in their natural state. According to Harborne (1967) the attached sugar may be glucose, galactose, arabinose, rhamnose, xylose, and many combinations of these sugars. The sugars are usually found in the 3, 5 and rarely in the 7 position of the molecule as defined above. The sugars impart stability and water solubility to the anthocyanin.

The aglycones, or sugar-free compounds are commonly known as anthocyanidins. The aglycones are insoluble in water, and tend to fade rapidly. Anthocyanins may be split up into anthocyanidins and sugar components by boiling in 20% hydrochloric acid for 3 minutes. The enzyme glucosidase has the same effect, splitting off the sugar and rendering the pigment less stable.

With few exceptions all anthocyanidins are hydroxylated in the 3, 5, and 7 positions, and fall into 3 major divisions; pelargonidin, cyanidin, and delphinidin, with 4, 5, and 6 hydroxyl groups respectively. The cyanidin group is most common in nature, followed by delphinidin and pelargonidin. In general the pelargonidins comprise the pink, scarlet, and orange red pigments, the cyanidins are crimson and magenta, while the delphinidins are mauve and blue. The basic structures may be represented as follows:

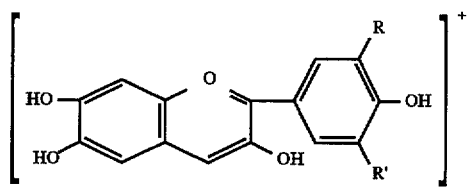

1. PELARGONIDIN R = R' = H
2. CYANIDIN R = OH
   R' = H
3. DELPHINIDIN R = R' = OH

The visible color of the anthocyanidins depends on the number and orientation of hydroxyl and methoxyl groups on molecules. Increasing numbers of hydroxyl groups are associated with deepening of color. Color is dependent on the solvent used; a given anthocyanin pigment is bluer in alcoholic solutions than in aqueous solutions. pH has a marked effect on the color of anthocyanins. As the pH of the pigment solution is raised to near neutrality the pigment is transformed into the colorless pseudo-base form (A→B), which may convent to the yellow chalkone form by the opening of the 3 carbon ring (B→C). As the pH is raised above 7 deep violet or purple anhydrous bases are formed (B→D). This form is unstable and degrades rapidly. Although these reactions are reversible, substantial pigment losses due to degradation occur while the pigment is held at higher pH's.

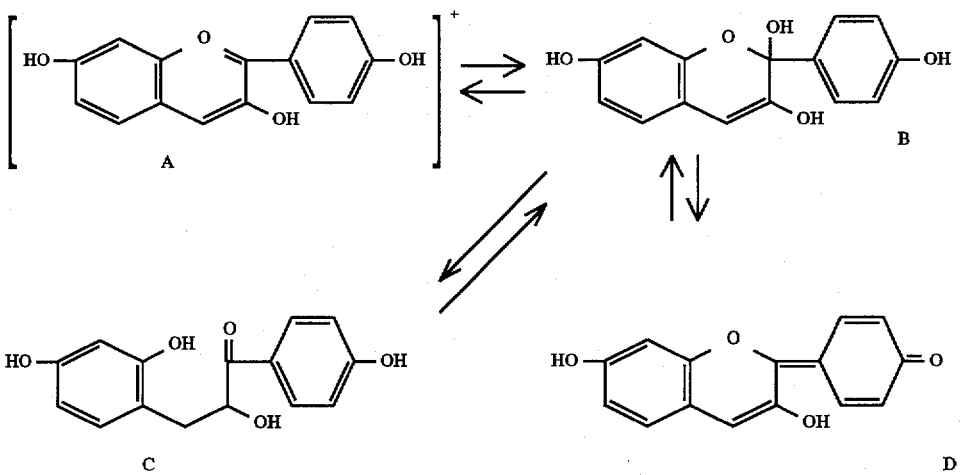

The anthocyanins of the cranberry, four in number, are cyanidin-3-galactoside, cyanidin-3-arabinoside, peonidin-3-galactoside, and peonidin-3-arabinoside.

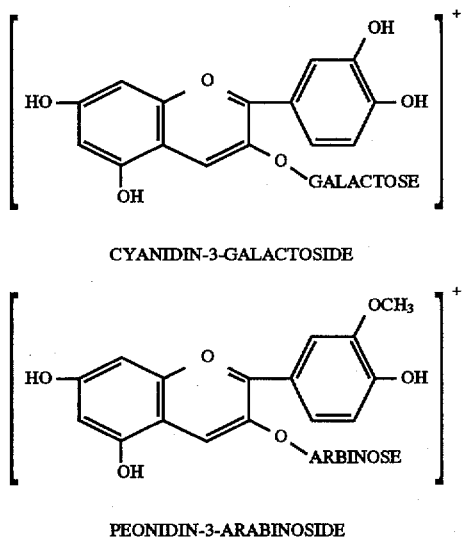

Acceptable Carrier

The carrier for the active component(s) can be any vehicle suitable for use in the oral cavity. Such carriers include the usual components of mouthwashes, toothpastes, tooth powders, prophylaxis pastes, lozenges, gums and the like and are more fully described hereinafter. Dentifrices and mouthwashes are the preferred systems.

In addition to the active agent(s), the present compositions may contain another antiplaque/gingivitis agent such as quaternary ammonium compounds, water insoluble agents such as triclosan, teas, as defined herein later, stannous salts and zinc salts. These types of agents are described in U.S. Pat. No. 4,894,220; Jan. 16, 1990 to Nabi et al, U.S. Pat. No. 4,656,031, Apr. 7, 1987 to Lane et al; and U.S. Pat. No. 5,004,597, Apr. 2, 1991 to Majeti et al. All incorporated herein by reference in their entirety.

The abrasive polishing material contemplated for use in the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and other such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride and polyphosphonates. For these reasons they are preferred for use herein.

The silica abrasive polishing materials useful herein, as well as the other abrasives, generally have an average particle size ranging between about 0.1 to 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975, both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, Jul. 29, 1982, incorporated herein by reference.

The abrasive in the compositions described herein is present at a level of from about 6% to about 70%, preferably from about 15% to about 25% when the dentifrice is a toothpaste. Higher levels, as high as 90%, may be used if the composition is a toothpowder.

Flavoring agents can also be added to dentifrice compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Dentifrice compositions can also contain emulsifying agents. Suitable emulsifying agents are those which are reasonably stable and foam throughout a wide pH range, including nonsoap anionic, nonionic, cationic, zwitterionic and amphoteric organic synthetic detergents. Many of these suitable surfactants are disclosed by Gieske et al. in U.S. Pat. No. 4,051,234, Sep. 27, 1977, incorporated herein by reference.

Water is also present in the toothpastes of this invention. Water employed in the preparation of commercially suitable toothpastes should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers of the type mentioned previously herein, xanthan gum, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols at a level of from about 15% to about 70%.

Another preferred embodiment of the present invention is a mouthwash composition. Conventional mouthwash composition components can comprise the carrier for the active agents of the present invention. Mouthwashes generally comprise from about 20:1 to about 2:1 of a water/ethyl alcohol solution and preferably other ingredients such as flavor, sweeteners, humectants and sudsing agents such as those mentioned above for dentifrices. The humectants, such as glycerin and sorbitol give a moist feel to the mouth. Generally, on a weight basis the mouthwashes of the invention comprise 0% to 60% (preferably 10% to 25%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to 0.3% (preferably 0.03% to 0.3%) flavoring agent, and the balance water.

Suitable lozenge and chewing gum components are disclosed in U.S. Pat. No. 4,083,955, Apr. 11, 1978 to Grabenstetter et al., incorporated herein by reference.

Other optional components useful in the present invention are pyrophosphate salts such as those described in U.S. Pat. No. 4,515,772, May 7, 1985 to Parran et al. incorporated herein by reference. Also useful are nonionic antimicrobials such as triclosan described in U.S. Pat. No. 4,894,220, Jan. 16, 1990 to Nabi et al. Both patents are incorporated herein by reference.

Another agent which can be used in the present compositions is an alkali metal bicarbonate, such as sodium bicarbonate. These are stable items of commerce and can be used together with a peroxide compound in separate compartments such as disclosed in U.S. Pat. No. 4,849,213 and U.S. Pat. No. 4,528,180, both to Schaeffer, incorporated herein by reference in its entirety.

The pH of the present compositions and/or its pH in the mouth can be any pH which is safe for the mouth's hard and soft tissues. Such pH's are generally from about 3 to about 10, preferably from about 4 to about 8.5.

METHOD OF MANUFACTURE

The carrier compositions of the present invention can be made using methods which are common in the oral products area.

For example, toothpaste compositions may be prepared by mixing part of the humectant and water together and heating to 66°–71° C. The fluoride source, if present, is then added along with the sweetener, the opacifier and the flavor. The cranberry extract may be combined with the glycerine prior to adding to the other components.

COMPOSITIONS USE

The present invention in its method aspect involves applying to the oral cavity safe and effective amounts of the compositions. Generally an amount of at least about 5 grams of a mouthwash and at least about 0.5 of a toothpaste or liquid dentifrice.

The following examples further describe and demonstrate preferred embodiments within the scope of the present invention. The examples are given solely for illustration and are not to be construed as limitations of this invention as many variations thereof are possible without departing from the spirit and scope thereof.

EXAMPLE I

Given below is a mouthrinse composition representative of the present invention:

| Component | Wt. % |
|---|---|
| Cranberry Extract | 1.25 |
| Glycerine | 12.00 |
| SD Alcohol | 14.00 |
| Distilled Water | 71.50 |
| Sodium saccharin | 0.15 |
| Monosodium Phosphate | 0.50 |
| Flavor (Herbal Alpine) | 0.10 |
| Pluronic F (68) | 0.50 |

EXAMPLE II

Given below is a dentifrice composition representative of the present invention:

| Component | Wt. % |
|---|---|
| Cranberry Extract | 5.00 |
| Glycerine | 19.00 |
| Sorbitol (70%) | 18.00 |
| Water | 6.91 |
| Sodium Fluoride | 0.24 |
| Sodium Saccharin | 0.15 |
| Monosodium Phosphate | 1.00 |
| Titanium Dioxide | 0.50 |
| Silica | 20.00 |
| Flavor | 0.90 |
| SAS (27.9% sol'n) | 4.00 |
| Fumed Silica | 2.00 |
| Sodium CMC | 0.30 |
| PEG 400 | 3.00 |
| Sorbital Solution | 19.00 |
| NaOH (50%) | (pH 6.5) |

In the above compositions, the cranberry extract level may be varied from about 0.005 grams to about 10 grams. Additionally, the compositions may contain secondary antiplaque/antigingivitis or anticaries components, such as black tea, oolong tea, green tea, quaternary ammonium compounds, water insoluble non-cationic compounds such as triclosan, and metal salts such as stannous salts and zinc salts. Furthermore, other members of the Ericaceae family may be used. Green, oolong, and black teas are members of the general tea family (Camillia Sinenis).

What is claimed is:

1. A toothpaste composition comprising:
   (a) a safe and effective amount of an active antimicrobial agent selected from the group consisting of an anthocyanin or anthocyaniden selected from the group consisting of cyandin, polar gonidin, and delphinidin, derivatives of these materials and mixtures thereof;
   (b) a silica dental abrasive; and
   (c) a soluble fluoride ion source.

2. A composition according to claim 1 wherein said composition contains a soluble pyrophosphate ion source as an anticalculus agent.

3. A composition according to claim 1 which contains another antiplaque agents selected from the group consisting of tea (Camillia Sinensis), metal salts, triclosan and mixtures thereof.

* * * * *

UNITED STATES PATENT AND TRADEMARK OFFICE
CERTIFICATE OF CORRECTION

PATENT NO. : 5,683,678

DATED : November 4, 1997

INVENTOR(S) : David Clinton Heckert, Richard Joseph Sunberg

It is certified that error appears in the above-identified patent and that said Letters Patent is hereby corrected as shown below:

Column 9, line 6 delete "polar" and insert -- pelar --

Signed and Sealed this

Fifteenth Day of December, 1998

Attest:

BRUCE LEHMAN

*Attesting Officer*  *Commissioner of Patents and Trademarks*